United States Patent [19]

Cecchi et al.

[11] Patent Number: 4,707,497

[45] Date of Patent: Nov. 17, 1987

[54] PHENYLETHANOLAMINOTETRALINES, A PROCESS FOR THEIR PREPARATION AND PHARMACEUTICAL COMPOSITIONS CONTAINING THEM

[75] Inventors: Roberto Cecchi; Robert Boigegrain; Alberto Bianchetti; Elena Poggesi; Tiziano Croci, all of Milan, Italy

[73] Assignee: Sanofi, Paris, France

[21] Appl. No.: 883,961

[22] Filed: Jul. 10, 1986

[30] Foreign Application Priority Data

Jul. 10, 1985 [FR] France ............................. 85 10559
May 7, 1986 [FR] France ............................. 86 06626

[51] Int. Cl.$^4$ .................. A61K 31/215; C07C 101/30
[52] U.S. Cl. .................................... 514/647; 514/510; 514/567; 560/45; 560/139; 562/452; 564/308
[58] Field of Search .................... 560/45, 252, 139; 562/452; 564/308; 514/510, 546, 567, 647

[56] References Cited

U.S. PATENT DOCUMENTS 4,035,512 7/1977 Sugihara et al. ...................... 560/45

OTHER PUBLICATIONS

Clark et al., *J. Pharm. Sci.*, vol. 75, No. 1, pp. 80–82, (1986).

*Primary Examiner*—Paul J. Killos
*Assistant Examiner*—Bruce D. Gray
*Attorney, Agent, or Firm*—Davis Hoxie Faithfull & Hapgood

[57] ABSTRACT

A novel phenylethanolaminotetraline having lipolytic activity of formula

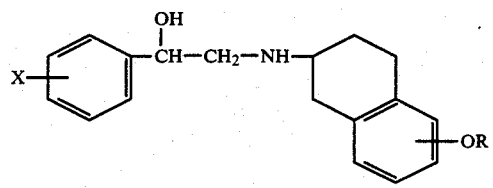

wherin X represents hydrogen, halogen, a trifluoromethyl or a lower alkyl group and R represents hydrogen, a lower alkyl group not substituted or substituted by a cycloalkyl group containing 3 to 7 carbon atoms, a hydroxy group, a lower alkoxy, carboxy or lower carbalkoxy group; a cycloalkyl group containing 3 to 7 carbon atoms; or a lower alcanoyl group; or a pharmaceutically acceptable salt thereof; a process for its preparation; and pharmaceutical compositions containing it as active ingredient, useful for the treatment of obesity.

8 Claims, No Drawings

PHENYLETHANOLAMINOTETRALINES, A PROCESS FOR THEIR PREPARATION AND PHARMACEUTICAL COMPOSITIONS CONTAINING THEM

The present invention relates to new phenylethanolaminotetralines having lipolytic activity, to a process for their preparation and to pharmaceutical compositions containing them as active ingredients.

It is known (Nature, 1979, 281, 31–35) that the Brown Adipose Tissue (BAT) and the White Adipose Tissue (WAT) have an important role in lipolysis and in thermogenesis; more particularly, themogenesis may have its metabolic origin in BAT.

It has also been demonstrated (Int. J. Obesity, 1984, 8, 159–180) that certain types of obesity are associated with a diminished ability to expend dietarily-derived energy as heat and that especially BAT is involved in the control of obesity, even though its role as an effector of dietary induced thermogenesis in rodents and in man remains to be unequivocally established.

It has now been found that certain phenylethanolaminotetralines and their salts posses a good stimulating activity on BAT and WAT and that they are useful for the treatment of obesity.

Thus, it is an object of the present invention to provide novel phenylethanolaminotetralines of formula:

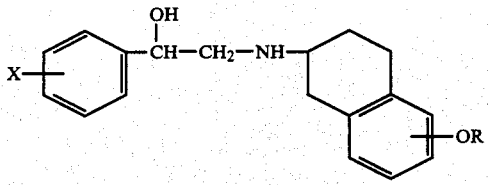

wherein X represents hydrogen, halogen, a trifluoromethyl or a lower alkyl group and R represents hydrogen; a lower alkyl group not substituted or substituted by a cycloalkyl group containing 3 to 7 carbon atoms, a hydroxy group, a lower alkoxy, carboxy or lower carbalkoxy group; a cycloalkyl group containing 3 to 7 carbon atoms; or a lower alcanoyl group; and their pharmaceutically acceptable salts.

The compounds of formula I above can be in an optically inactive form or in an optically active form selected from the group consisting of the enantiomers, the diastereoisomers and mixtures thereof. All these compounds and their pharmaceutically acceptable salts are included in the scope of the present invention.

The term "lower alkyl", as used herein, designates a monovalent radical of a saturated hydrocarbon containing 1 to 4 carbon atoms, such as methyl, ethyl, propyl, isopropyl or n-butyl.

The terms "lower alkoxy" and "lower carbalkoxy" designate the hydroxyl and carboxyl groups, respectively, etherified and esterified, respectively, with a lower alkyl as defined above.

The term "lower alkanoyl" designates a carbonyl group substituted by a lower alkyl as defined above.

The term "halogen" includes the four halogens fluorine, chlorine, bromine, iodine, the first three being particularly preferred.

The compounds of formula I and their pharmaceutically acceptable salts have a remarkable lipolytic activity and may be used for the treatment of obesity.

It is another object of the present invention to provide a process for the preparation of compounds of formula 1 and of pharmaceutically acceptable salts thereof.

Said process comprises reacting a compound of formula

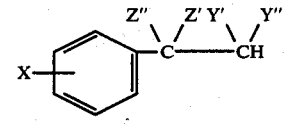

wherein X is as defined above; one of Z' and Z" is hydrogen and the other is a hydroxy group or Z' and Z", together, form an oxo group; one of Y' and Y" is hydrogen and the other is a halogen selected from the group consisting of chlorine, bromine and iodine or an amino group or Y' and Y", together form an oxo group; or, both Y" and Z" are hydrogen and Y' and Z', together, form an epoxy oxygen atom; with a tetraline, having its optional hydroxy and carboxy substituents optionally protected, of formula

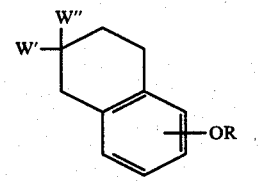

wherein R is as defined above and either one of W' and W" is hydrogen and the other is an amine group or W' and W''', together, form an oxo group; the reaction being carried out, when at least an oxo group is present in one of the compounds II and III, in the presence of a reducing agent; then optionally separating the stereoisomeres of the compounds of formula I; eliminating the optionally present protecting groups; and optionally converting the product thus obtained into its pharmacetically acceptable salts; with the proviso that in the reacting compounds II and III when Y' or Y" is an amino group, one of W' and W" is other than an amino group, when Y' and Y", together, form an oxo group, then W' and W''', together, are other than oxo group, and when Y' and Z', together, form an epoxy oxygen atom, then W' and W''', together, are other than oxo group.

In the starting tetraline of formula III, the hydroxy and the carboxy groups which are optionally present may be free or protected.

The protecting group of the hydroxy group includes an acyl group such as, for example, formyl, acetyl, chloroacetyl, trifluoroacetyl, methoxyacetyl, phenoxyacetyl, benzoyl, benzoyformyl, p-nitro-benzoyl, athoxycarbonyl, beta,beta,beta-trichloroethoxycarbonyl, beta,beta,beta-tribromoethoxycarbonyl or p-nitrophenoxycarbonyl or a protecting group which may be easily eliminated under relatively mild hydrolysis conditions such as, for example, a tetrahydropyranyl, tetrahydrothiofuranyl or methoxytatrahydropyranyl group or a protecting group that may be eliminated by catalytic hydrogenation, such as benzyl, benzhydryl, methoxybenzyl, trityl.

The phenolic hydroxy group may be also protected by a lower alkyl group.

The carboxy group is generally protected under the form of one of its esters.

The protected hydroxy groups may be split according to conventional techniques. Thus, the aromatic methoxy group may be converted into the corresponding phenol according to the known demethylation methods, for example by treatment with a boron trifluoride or tribromide complex such as boron tribromide/dimethylsulfide. The benzyloxy, benzhydryloxy, methoxybenzyloxy and trityloxy groups may be split by carslytic hydrogenation.

The alkanoyloxy groups, such as the formyloxy and acetoxy groups give the corresponding free hydroxy group according to the known saponification methods.

Analogously, the carbalkoxy groups are converted into the corresponding carboxy groups by saponification.

Even though the protection of the hydroxy and carboxy groups of the tetraline III is not necessary, it may be useful in case of better availability of the starting material or for a better accomplishment of the reaction. For example, 6- and 7-methoxy-2-tetralone are more available than 6- and 7-hydroxy-2-tetralone and esters of carboxylic acids are more soluble in organic solvents than the corresponding free acids.

A preferred embodiment of the process of the present invention comprises reacting a racemic or optically active phenylethanolamine of formula:

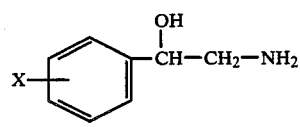

IIa wherein X is as defined above, with a tetralone, having its optional hydroxy and carboxy substituents optionally protected, of formula:

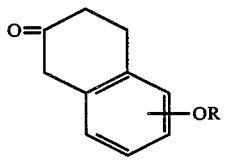

IIIa wherein R is as defined above in an organic solvent in the presence of a reducing agent; optionally separating the stereoisomeres of compounds of formula I, advantageously by fractional crystallization in an appropriate solvent or by chromatography, then eliminating the optionally present protecting groups and optionally converting the product thus obtained into one of its pharmaceutically acceptable salts.

As preferred organic solvent, an aliphatic alcohol of from 1 to 6 carbon atoms is used, such as methanol, ethanol, n-butanol, n-pentanol but other solvents such as hexane, benzene and toluene may be used.

According to this method of preparation, involving a reductive amination, the reaction is carried out in the presence of hydrogen and of a suitable catalyst, such as, for example, platinum bioxyde, Nickel-Raney or palladium or charcoal, or in the presence of another reducing agent, for example an organic reducing agent, such as sodium cyanoborohydride, sodium borohydride, tetrabutylammonium cyanoborohydride, lithium cyanoborohydride or lithium triethylborohydride.

The reaction is advantageously carried out in the presence of an organic acid, such as, for example, glacial acetic acid.

The reaction temperature may vary from the room temperature (about 20° C.) to 50° C., preferably from 30° to 40° C. and the time varies consequently. Generally, after 3-6 hours of heating at 30°-40° C., the reaction is over and the final product thus obtained may be isolated according to the conventional technique.

Another advantageous embodiment of the process of the present invention comprises reacting an epoxy compound of formula

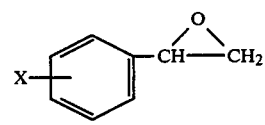

IIb wherein X is as defined above, with an aminotetraline, having its optional hydroxy and carboxy substituents optionally protected, of formula:

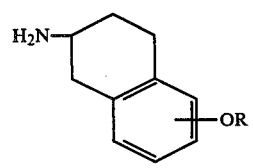

IIIb wherein R is as defined above.

The reaction may be carried out in the absence of solvents or in the presence of an organic solvent. Generally, after 5-96 hours at a temperature of from 0° to 50° C., the reaction is complete and the product thus obtained is isolated, optionally deprotected and optionally converted into a salt thereof.

Another advantageous embodiment of the process of the present invention comprises reacting a phenlglyoxal of formula

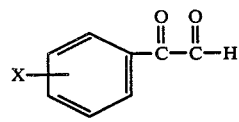

IIc wherein X is as defined above, with an aminotetraline, having its optional hydroxy and carboxy substituents optionally protected, of formula IIIb in the presence of a reducing agent.

The reaction is carried out in an organic solvent, generally at room temperature (about 20° C.).

The reducing agents include those described above, for example sodium borohydride.

The product of formula I is isolated, optionally deprotected and optionally converted into a salt thereof.

Another advantageous embodiment of the process of the present invention comprises reacting an alpha-haloacetophenone of formula

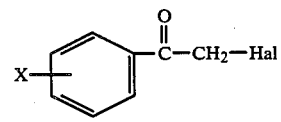

IId wherein X is as defined above and Hal is selected from the group consisting of chlorine, bromine and iodine, with an aminotetraline, having its optional hydroxy and carboxy substituents optionally protected, of formula IIIb in the presence of a reducing agent.

The reaction conditions are the same as described above. However, since an hydrogen halide liberates, it is advantageous to neutralize it with a tertiary amine such as triethylamine, to isolate the ketone and to carry out the reduction on the isolated product. The phenylethanolaminotetraline thus obtained may be isolated, optionally deprotected and optionally transformed in its salts.

A preferred starting alpha-haloacetophenone of formula IId is alpha-bromoacetophenone.

The compounds of formula I present two asymmetric carbon atoms.

According to a further embodiment of the present invention, the mixtures of diasteroisomers are obtained by crystallization in a suitable solvent, preferably a lower alkanol such as isopropyl alcohol, ethanol or their mixtures. The stereoisomers may be obtained from these mixtures according to known procedures, for example by chromatographic separation or by reaction with an optically active acid to form salts which may be separated. The optically active acids useful for the resolution procedures are described in Topics in Stereochemistry, vol. 6, Wiley Interscience 1971, Allinger N.L. and Eliel W.L. eds.

Stereoisomers may also be obtained starting from one of the enantiomers of a phenylethanolamine of formula IIa by reaction with a compound of formula IIIa and reduction. The diasteroisomers thus obtained may be separated according to known techniques such as by fractional crystallization in a suitable solvent, preferably a lower alkanol, such as isopropyl alcohol, ethanol or their mixtures.

Stereoisomers may further be obtained starting from one of the enantiomers of an aminotetraline of formula IIIb by reaction with a compound of formula IIb, IIc or IId and isolated as described above.

Pure stereoisomers may finally be obtained starting from one of the enantiomers of an epoxyde of formula IIb with one of the enantiomers of an aminotetraline of formula IIIb.

For the nomenclature of the racemates, as well as for the stereoisomers and the mixtures thereof, the following convention is adopted hereinafter:

the products obtained starting from racemates are defined by their chemical name without any designation of the stereochemistry;

the mixtures of diasteroisomers obtained starting from one of the enantiomers of either a compound II or a compound III are defined "(1R,2'RS)", "(1S,2'RS)", "(1RS,2'R)" and "(1RS,2'S)", respectively;

the stereoisomers of which only one center of asymmetry has a known configuration are defined by the sign (+) or (−) of the optical rotation and by the configuration of the sole defined center.

The compounds of formula I may be converted into their pharmaceutically acceptable salts.

When the compound of formula I is in the form of the free base, the salification is carried out by treatment with the selected acid in an organic solvent.

When the compound of formula I possess a free carboxy group, its amphoteric character allows the preparation of salts either with acids or with bases. The salts with pharmaceutically acceptable bases are preferably those with alkali metals such as sodium, but the salts with organic bases, such as the salt with trometamol, are advantageous too.

Pharmaceutically acceptable acid addition salts are obtained by treating the free base, dissolved for example in an alcohol such as isopropyl alcohol, with a solution of the chosen acid in the same solvent. The corresponding salt is isolated according to the conventional techniques. Thus, for example, the hydrochloride, the hydrobromide, the sulfate, the hydrogen sulfate, the dihydrogen phosphate, the methanesulfonate, the methylsulfate, the oxalate, the maleate, the fumarate, the naphthalene-2-sulfonate are prepared.

At the end of the reaction of compound II with compound II, the compound of formula I may be isolated in the form of one of its salts, for example the hydrochloride; in this case, if it is necessary, the free base may be prepared by neutralising said salt with a mineral or organic base, such as sodium hydroxyde or triethylamine or an alkali metal carbonate or bicarbonate, such as sodium or potassium carbonate or bicarbonate.

The compounds of formula I and their salts possess interesting pharmacological properties. More particularly, the compounds of the present invention show a remarkable lipolytic activity in mammals in the tests predictive of said activity, such as in the test "in vitro" on the brown adipose tissue (BAT) and on the white adipose tissue (WAT) and in the test "in vivo", based upon the thermogenesis in the rat.

More particularly, in the test "in vitro" male rats, each weighing 100–125 g, are sacrificed and the adipocytes of the interscapular brown adipose tissue and those of the epididymal white adipose tissue are dissected out, according to the method of M. Rodbell, J. Biol. Chem. 1967, 242, 5744–5750 and separately treated as follows. The adipocytes are incubated with the compound to be tested at a temperature of 37° C. for an hour in Phosphate Krebs-Ringer-(4%) albumine medium at pH 7.4. The long chain fatty acids that are released in the medium are determinated by the method reported by D.I. Trout and al., J. Lip. Res. 1960, 1, 199–202, and compared with the amount of the triglycerides present in the adipocytes, determined by the method of E. Van Handel and al., J. Lab. Clin. Med., 1957, 50, 152–157.

The results obtained for representative compounds of the present invention are shown in TABLE I, where the lipolytic activity of the compounds at the dose of $10^{-6}$ M, measured as release of free fatty acids ($\mu$Eq), is expressed as per cent of the noradrenaline effect at the dose of $5.10^{-6}$ M (maximal effect on both BAT and WAT).

TABLE I

| Compound ($10^{-6}$ M) | Example No | Lipolytic activity BAT | Lipolytic activity WAT |
|---|---|---|---|
| SR 58279A | 1 | 50% | 30% |
| SR 58306A | 4 | 80% | 78% |
| SR 58338A | 7 | 77% | 89% |
| SR 58339A | 8 | 103% | 92% |
| SR 58365A | 18 | 96% | 78% |
| SR 58375A | 22 | 100% | 97% |
| SR 58380A | 11 | 96% | 90% |

In the test "in vivo", the activity on brown adipose tissue thermogenesis is determined by the method reported by P. J. Wellman, Research Communication in Chemical Pathology and Pharmacology 1983, 41, 173–176.

The anaesthesied rats are treated intraperitoneally with the vehicle and 7.5 mg/kg of the compound to be tested. The interscapular BAT and rectal temperatures are recorded 10, 20 and 30 minutes after the injection.

TABLE II shows the average difference ($\Delta T$) between the interscapular BAT temperature and the rectal temperature of the animals treated with a representative compound of the present invention and of the controls having received the vehicle only.

TABLE II

| Compound 7.5 mg/kg (intraperitoneally) | $\Delta T$ °C. Time | | |
|---|---|---|---|
| | 10' | 20' | 30' |
| Vehicle | 0.06 ± 0.04 | 0.10 ± 0.04 | 0.14 ± 0.05 |
| SR 58306 (Ex.3) | 0.60 ± 0.10 | 0.90 ± 0.10 | 0.92 ± 0.08 |

The results obtained in the tests in "in vitro" and "in vivo" show that the representative compounds of the invention have a remarkable lipolytic activity, both on the BAT and on the WAT and that they activate the thermogenesis in BAT of anaesthetized rats significantly.

The compounds of formula I above and their pharmaceutically acceptable salts are also modulators of the intestinal and uterine motility as shown in the tests of the rat colon and uterus and in the test of the gastrointestinal motility in dogs.

In addition, the compounds of the present invention are practically inactive as beta-1 or beta-2 adrenergic stimulants as shown in the classical tests of the isolated right atrium and trachea of guinea pigs.

The compounds of formula I above and their pharmaceutically acceptable salts are only slightly toxic; their LD50 in mice varies from 15 to 35 mg/kg intravenously and may be higher than about 350 mg/kg orally; for example, the compounds SR 58380 A (Example 11) and SR 58339 A (Example 8) do not cause any mortality in mice up to an oral dose up to 200 mg/kg.

Thus, it is another object of the present invention to provide pharmaceutical compositions particularly useful for the treatment of obesity containing, as active ingredients, the compounds of formula I above, as well as their pharmaceutically acceptable salts.

In the pharmaceutical compositions of the present invention, for oral, sublingual, sub-cutaneous, intramuscular, intravenous, transdermic or rectal administration, the active ingredients of formula I above may be administered in unit forms of administration, in admixture with conventional pharmaceutical carriers, to animals and human beings for the treatment of obesity. Appropriate unit forms of administration include the forms for oral administration, such as tablets, capsules, powders, granulates and oral solutions or suspensions and the forms for sublingual and buccal administration, the forms for parenteral administration useful for a subcutaneous, intramuscular or intravenous injection, as well as the forms for rectal administration.

In order to obtain the desired lipolytic effect, the dose of active ingredient may vary between 0.01 and 100 mg per kg of body weight and per day.

Each unit dose may contain from 0.1 to 500 mg of active ingredient, in admixture with a pharmaceutical carrier. This unit dose may be administered from 1 to 4 times daily.

When a solid composition is prepared in the form of tablets, the main active ingredient is mixed with a pharmaceutical excipient such as gelatine, starch, lactose, magnesium stearate, talc, arabic gum and the like. The tablets may be coated with sucrose or other appropriate materials or they may be treated so that their activity is extended or delayed and that they continually release a predetermined amount of active ingredient.

A preparation in capsules is obtained by mixing the active ingredient with a diluent and by pouring the mixture obtained in soft or hard capsules.

A liquid preparation in the form of syrup or elixir or for the administration in drops may contain the active ingredient jointly with a possibly acaloric sweetening agent, methylparaben and propylparaben as antiseptics, as well as a flavoring agent and an appropriate dye.

Water-dispersible powders or granulates may contain the active ingredient mixed with dispersing agents or wetting agents, or suspending agents such as polyvinylpyrrolidone and the like, and with sweetening or flavoring agents.

For rectal applications, suppositories are prepared with binding agents melting at rectal temperature, for example, cocoa butter or polyethyleneglycols.

For parenteral administration, aqueous suspensions, isotonic saline solutions or sterile injectable solutions are used, which contain pharmacologically compatible dispersing and/or wetting agents, for example propyleneglycol or butyleneglycol.

The active ingredient may also be formulated in the form of microcapsules, possibly with one or more supports or additives.

The compositions of the present invention may contain, beside the compounds of formula I above or one of their pharmaceutically acceptable salts, other active ingredients, such as, for example, anorectics, tranquillizers, antidepressants or other drugs useful in the treatment of obesity.

The following examples illustrate the invention without, however, limiting it. The rotation power values are the results of only one determination. They are indicated as [alpha], but they must be read $[alpha]_D^{25}$.

EXAMPLE 1

(a) An amount of 1 g of 7-methoxy-2-tetralone is reacted at 35° C. for 4 hours with 0.8 g of 2-amino-1-phenylethanol in 30 ml of methanol and 1 ml of glacial acetic acid in the presence of hydrogen and 0.1 g of platinum bioxide. After filtration and concentration, the residue is taken up with water, made alkaline with concentrated sodium hydroxyde and extracted with ethyl acetate. The solution is dried over anhydrous sodium sulfate, evaporated to dryness, then the residue is dissolved in isopropyl alcohol. To the solution thus obtained, there is added a saturated solution of hydrogen chloride in isopropyl alcohol. Thus there is obtained the 2-8(7-2-((1-methoxy-1,2,3,4-tetrahydronaphth-2-yl)amino]-1-phenylethanol hydrochloride, designated by its code number SR 58279 A, which after crystallization from isopropyl alcohol, melts at 185°-187° C. Yield: 37% of the theoretical value.

(b) An amount of 3.01 g of 2-amino-7-methoxy-1,2,3,4-tetrahydronaphthalene is reacted under stirring at room temperature for 4 days with 2.04 g of styrene. After addition of ethyl acetate, to the reaction mixture there is added a saturated solution of hydrogen chloride in isopropyl alcohol to obtain the 2-[(7-methoxy-1,2,3,4-tetrahydronaphth-2-yl)amino]-1-phenylethanol hydrochloride. Yield: 31% of the theoretical value.

(c) An amount of 3.53 g of phenylglyoxal is reacted under stirring at room temperature for 3 hours with 5 g of 2-amino-7-methoxy-1,2,3,4-tetrahydronaphthalene hydrochloride in 100 ml of methanol in the presence of 0.9 g of sodium borohydride. After cooling to 4° C., 4,3 g of sodium borohydride are added and the reacting mixture is left under stirring at room temperature for a night. After addition of 20 ml of water, the solution is stirred at room temperature for 15 minutes, then it is evaporated to dryness. The residue is dissolved in 300 ml of ethyl acetate and 60 ml of water; after filtration, the organic phase is separated, dried over magnesium sulfate, filtered and evaporated to dryness. The oil thus obtained is purified by flash-chromatography by using a mixture ethyl acetate/methanol 8/2 as eluant to obtain the 2-[(7-methoxy-1,2,3,4-tetrahydronaphth-2-yl)amino]-1-phenylethanol hydrochloride. Yield: 20% of the theoretical value.

(d) To a mixture of 1.77 g of 2-amino-7-methoxy-1,2,3,4-tetrahydronaphthalene and 1.1 g of triethylamine in 25 ml of tetrahydrofurane, there is added slowly 1.94 g of bromoacetophenone in 50 ml of tetrahdryofurane. The reaction mixture is left under stirring at room temperature for 2 hours, then is filtered andevaporated. The residue thus obtained is dissolved in isopropyl alcohol and acidified with a solution of hydrogen chloride in isopropyl alcohol, then it is precipitated with an etheral solution, filtered and dried. To the solution of the residue in 70 ml of methanol, cooled to 4° C., there is added slowly 1.5 g of sodium borohydride. The reaction mixture is stirred at room temperature for an hour, poured into water and acidified with acetic acid. The solution is made alkaline with sodium bicarbonate and the organic phase is extracted with methylene chloride, dried and evaporated to dryness. The oil thus obtained is purified by flash-chromatography using a mixture ethyl acetate/methanol 8/2. After recrystallization from isopropyl alcohol, the 2-[(7-methoxy-1,2,3,4-tetrahydronaphth-2-yl)amino]-1-phenylethanol hydrochloride is obtained. Yield: 30% of the theoretical value.

EXAMPLE 2

An amount of 4 g of 6-methoxy-2-tetralone is reacted at 35° C. for 3 hours with 3.2 g of 2-amino-1-phenylethanol in 100 ml of methanol and 4 ml of glacial acetic acid in the presence of hydrogen and 0.3 g of platinum bioxide. After filtration and concentration, the residue is taken up with sodium hydroxide and extracted with ethyl acetate. The solution is dried over anhydrous sodium sulfate and evaporated. The black oil thus obtained is purified by flash-chromatography by utilizing a mixture of methylene chloride/methanol 9/1 as eluant. The fractions containing the product are collected and evaporated to dryness. The residue is dissolved in 20 ml of isopropyl alcohol and to the solution thus obtained there is added a saturated solution of hydrogen chloride in isopropyl alcohol. Thus, there is obtained the 2-[(6-methoxy-1,2,3,4-tetrahydronaphth-2-yl)amino]-1-phenylethanol hydrochloride, designated by its code number SR 58280 A, which, after crystallization from isopropyl alcohol, melts at 174°-176° C. Yield: 47.5% of the theoretical value.

EXAMPLE 3

An amount of 3.3 g of 2-[(7-methoxy-1,2,3,4-tetrahydronaphth-2-yl)amino]-1-phenylethanol hydrochloride (SR 58279 A), obtained as described in Example 1, is refluxed under a nitrogen stream for 16 hours with a mixture of 9.5 g of the boron tribromide/dimethylsulfide complex and 100 ml of anhydrous methylene chloride. The solution thus obtained is cooled, treated with ethyl acetate and water made alkaline with a saturated solution of sodium bicarbonate. The solution is extracted with ethyl acetate and, after drying over magnesium sulfate, is filtered and evaporated to dryness. The doughy solid product thus obtained is purified by flash-chromatography by utilizing a mixture chloroform/methanol 8/2 as eluent. After two crystallizations from 7 ml of ethyl acetate the 2-[(7-hydroxy-1,2,3,4-tetrahydronaphth-2-yl)amino]-1-phenylethanol, designated by its code numbers SR 58306, is obtained; m.p. 156°-158° C. Yield: 60% of hte theoretical value. The product contains the two diasteroisomers (1R, 2'R;1S,2'S) and (1R,2'S;1S,2'R) in the ratio of about 1/1 (determinated by NMR at 250 MHz).

EXAMPLE 4

To a solution in isopropyl alcohol of 1.7 g of 2-[(7-hydroxy-1,2,3,4-tetrahydronaphth-2-yl)amino]-1-phenylethanol, obtained as described in Example 3, there is added hydrochloric acid in isopropyl alcohol. After precipitation with ethyl ether, the 2-[(7-hydroxy-1,2,3,4-tetrahydronaphth-2-yl) amino]-1-phenylethanol hydrochloride, designated by its code number SR 58306 A, is obtained, which, after drying, melts at 157°-159° C. Yield: 56% of the theoretical value.

EXAMPLE 5

An amount of 3.9 g of 2-[(7-hydroxy-1,2,3,4-tetrahydronaphth-2-yl)amino]-1-phenylethanol, obtained as described in Example 3, in 40 ml of dimethylsulfoxide and in the presence of 0.63 g of sodium hydride dispersed in oil (55%) is stirred for 30 minutes at toom temperature. After addition of 2.1 ml (0.0137 mole) of ethyl bromoacetate, the reaction mixture is left to stand at room temperature for 3 hours and 30 minutes. Then it is poured into 300 ml of water and extracted with 300 ml of ethyl acetate, dried, filtered and evaporated to dryness. Thus, an oil is obtained which is purified by flash-chromatography using a mixture ethyl acetate/methanol 95/5 for the elution. The oil purified is left to react for a night with an excess of oxalic acid in 5 ml of isopropyl alcohol to obtain the 2-[(7-carbethoxymethoxy-1,2,3,4-tetrahydronaphth-2-yl)amino]-1 phenylethanol oxalate, designated by its code number SR 58436 A; m.p. 159°-162° C. Yield: 5% of the theoretical value.

EXAMPLE 6

An amount of 1.5 g of 2[(6-methoxy-1,2,3,4-tetrahydronaphth-2-yl)amino]-1-phenylethanol hydrochloride, obtained as described in Example 2, is refluxed 16 hours under a nitrogen stream, in a solution of 4.3 g of the boron tribromide/dimethylsulfide complex in 80 ml of anhydrous methylene chloride. The solution is cooled, then it is treated with ethyl acetate and water made alkaline with a saturated solution of sodium bicarbonate. The solution is extracted with with ethyl acetate, dried over magnesium sulfate, filtered and evaporated to dryness. The product thus obtained is dissolved in isopropyl alcohol and the solution is made acid with hydrogen chloride in isopropyl alcohol. The product is precipitated by adding ethyl ether to obtain the 2-[(6-hydroxy-1,2,3,4-tetrahydronaphth-2-yl)amino]-1-phenylethanol hydrochloride, designated by its code number SR 58307 A, which, after drying, melts at 166°-168° C. Yield: 35% of the theoretical value.

EXAMPLE 7

A mixture of 4.8 g of 2-amino-1-(3-chlorophenyl)ethanol and 5 g of 7-methoxy-2-tetralone in 80 ml of methanol and 5 ml of glacial acetic acid is stirred at room temperature for three hours. Then 2.7 g of sodium cyanoborohydride are added thereto and the solution thus obtained is left under stirring for a night. The mixture is made acid and evaporated to dryness, then the residue is taken up with 40 ml of water made alkaline and extracted with 200 ml of ethyl acetate. The organic phase thus obtained is dried over anhydrous sodium sulfate, filtered and evaporated to dryness. The oil thus obtained is purified by flash-chromatography using a mixture ethyl acetate/methanol 95/5 for the elution. To the solution thus obtained there is added 40 ml of isopropyl alcohol and 150 ml of ethyl ether, then some drops of isopropyl alcohol saturated with hydrogen chloride. Thus, there is obtained the 2-[(7-methoxy-1,2,3,4-tetrahydronaphth-2-yl)amino]-1-(3-chloropheny)ethanol hydrochloride, designated by its code number SR 58338 A, which, after crystillization from isopropyl alcohol, melts at 186°–188° C. Yield: 40% of the theoretical value.

EXAMPLE 8

To a suspension of 3.7 g of 2-[(7-methoxy-1,2,3,4-tetrahydronaphth-2-yl)amino]-1-(3-chlorophenyl) ethanol hydrochloride, obtained as described in Example 7, in 60 ml of anhydrous methylene chloride, there is added dropwise, under a nitrogen stream and at the temperature of −20° C., 60 ml of a 1M solution of boron tribromide in methylene chloride. The reaction mixture is left under stirring at the temperature of −20° C. for 3 hours and 30 minutes. An excess of ice is added and the mixture is made alkaline with concentrated ammonia. The organic phase is separated, dried over anhydrous sodium sulfate and evaporated to dryness. The residue thus obtained is purified by flash-chromatography using a mixture of methylene chloride/methanol 9/1 for the elution. The 2-[(7-hydroxy-1,2,3,4-tetrahydronaphth-2-yl)amino]-1-(3-chlorophenyl)ethanol, thus obtained in the form of basis, is dissolved in a mixture of 10 ml of isopropyl alcohol and 30 ml of ethyl ether. To the resulting solution there is added a saturated solution of hydrogen chloride in isopropyl alcohol to obtain the 2-[(7-hydroxy-1,2,3,4-tetrahydronaphth-2-yl)amino]-1-(3-chlorophenyl)-ethanol hydrochloride, designated by its code number SR 58339 A, which, after crystallization from 20 ml of absolute ethanol, melts at 113°–115° C. Yield: 30% of the theoretical value.

EXAMPLE 9

By addition to the basis obtained as described in Example 8, of a 48% solution of hydrobromic acid in water, the 2-[(7-hydroxy-1,2,3,4-tetrahydronaphth-2-yl)amino]-1-(3-chlorophenyl)ethanol hydrobromide, designated by its code number SR 58339 B, is obtained; m.p. 126°–128° C. Yield: 65% of the theoretical value.

EXAMPLE 10

By addition to the basis obtained as described in Example 8 of a solution of fumaric acid in water, the 2-[(7-hydroxy-1,2,3,4-tetrahydronaphth-2-yl)amino]-1-(3-chlorophenyl)ethanol fumarate, designated by its code number SR 58339 C, is obtained; m.p. 223°–225° C. Yield: 56% of the theoretical value.

EXAMPLE 11

A solution of 7.1 g of 2-[(7-hydroxy-1,2,3,4-tetrahydronaphth-2-yl)amino]-1-(3-chlorophenyl)ethanol hydrochloride, obtained as described in Example 8, in 50 ml of dimethylsulfoxide is left under stirring at room temperature for 30 minutes in the presence of 1.9 g of 55% sodium hydride dispersion in oil (FLUKA). The reacting mixture is treated with 3.3 g of ethyl bromoacetate and left under stirring at room temperature for 24 hours. The solution thus obtained is poured into 300 ml of water, extracted with 300 ml of ethyl acetate, the organic phase is dried over sodium sulfate, filtered and evaporated to dryness. The oil thus obtained is purified by flash-chromatography using a mixture ethyl acetate/methanol 95/5 for the elution. The oil purified is left to react for 36 hours with an excess of oxalic acid in 20 ml of isopropyl alcohol to obtain the 2-[(7-carbethoxymethoxy-1,2,3,4-tetrahydronaphth-2-yl) amino]-1-(3-chlorophenyl)ethanol oxalate, designated by its code number SR 58380 A; m.p. 145°–147° C. Yield: 5% of the theoretical value.

EXAMPLE 12

A mixture of 8.5 g of D(−)phenylethanolamine (J. Org. Chem. 1980, 45, 2785) and 12 g of 7-methoxy-2-tetralone in 150 ml of methanol is left to react under stirring at room temperature for 3 hours in the presence of 9 ml of glacial acetic acid. The reacting mixture is left under stirring at room temperature for a night in the presence of 5.8 g of sodium cyanoborohydride, then it is made acid at pH 3 with concentrated hydrochloric acid and left under stirring at room temperature for 30 minutes. The mixture is evaporated to dryness, the residue is taken up with 80 ml of water and made alkaline with concentrated ammonia. The organic phase is extracted with 400 ml of ethyl acetate, washed with 40 ml of water, dried over anhydrous sodium sulfate, filtered and evaporated to dryness. The product thus obtained is purified by flash-chromatography using a mixture ethyl acetate/methanol 9/1 as eluant. The product is dissolved in 70 ml of isopropyl alcohol, to the solution thus obtained there is added a saturated solution of hydrogen chloride in isopropyl alcohol to obtain the (1R,2′RS)-2-[(7-methoxy-1,2,3,4-tetrahydronaphth-2-yl)amino]-1-phenylethanol hydrochloride, designated by its code number SR 58361 A, m.p. 195°–199° C., [alpha]=−30° (water/ethanol 1/1, c=2%). Yield: 43.5% of the theoretical value. The product contains the two diasteroisomers (1R,2′R) and (1R,2′S) in the ratio of about 1/1 (determinated by HPLC).

EXAMPLE 13

By following the procedure of Example 12, starting from 14 g of L(+)phenylethanolamine (J. Org. Chem. 1980, 45, 2785) and 19.8 g of 7-methoxy-2-tetralone, there is obtained the (1S,2′RS)-2-[(7-methoxy-1,2,3,4-tetrahydronaphth-2-yl)amino]-1-phenylethanol hydrochloride designated by its code number SR 58358 A, m.p. 194°–198° C., [alpha]=+28° (water/ethanol 1/1, c=2%). Yield: 47.6% of the theoretical value.

The product contains the two diasteroisomers (1S,2′R) and (1S,2′S) in a ratio of about 1/1 (determinated by HPLC)

EXAMPLE 14

Six grams of the (1R,2′RS)-2-[(7-methoxy-1,2,3,4-tetrahydronaphth-2-yl)-amino]-1-phenylethanol hydrochloride, obtained as described in Example 12, are crystallized four times from a mixture isopropyl alcohol/95% ethanol 6/4. The mother-liquors of the crystallization are collected and evaporated to dryness. The product obtained is crystallized from 40 ml of absolute ethanol. The mother-liquors of this last crystallization are evaporated and their residue triturated in 20 ml of ethyl ether. The (−)-(1R)-2-[(7-methoxy-1,2,3,4-tetrahydronaphth-2-yl) amino]-1-phenylethanol hydrochloride, designated by its code number SR 58362 A, is thus obtained, m.p. 169°–171° C., [alpha]=−92° (water/ethanol 1/1, c=2%). Yield: 25% of the theoretical value.

EXAMPLE 15

By following the procedure of Example 14, starting from 11 g of (1S,2′RS)-2-[(7-methoxy-1,2,3,4-tetrahydronaphth-2-yl)amino]-1-phenylethanol hydrochloride, obtained as described in Example 13, the (+)-(1S)-2-[(7-methoxy-1,2,3,4-tetrahydronaphth-2-yl)amino]-1-phenylethanol hydrochloride, designated by its code number SR 58359 A, is obtained, m.p. 172°–175° C., [alpha]=+95° (water/ethanol 1/1, c =2%). Yield: 20% of the theoretical value.

EXAMPLE 16

Six grams of (1R,2′RS)-2-[(7-methoxy-1,2,3,4-tetrahydronaphth-2-yl)-amino]-1-phenylethanol hydrochloride, obtained as described in Example 12, are crystallized six times from a mixture of isopropyl alcohol/95% ethanol 6/4. The (+)-(1R)-2-[(7-methoxy-1,2,3,4-tetrahydronaphth-2-yl)amino]-1-phenylethanol hydrochloride, designated by its code number SR 58363 A, is obtained, m.p. 220°–222° C., [alpha]=+32° (water/ethanol 1/1, c =2%). Yield: 30% of the theoretical value.

EXAMPLE 17

By following the procedure of Example 16, starting from 11 g of (1S,2′RS)-2-[(7-methoxy-1,2,3,4-tetrahydronaphth-2-yl)amino]-1-phenylethanol hydrochloride, obtained as described in Example 13, the (−)-(1S)-2-[(7-methoxy-1,2,3,4-tetrahydronaphth-2-yl)amino]-1-phenylethanol hydrochloride, designated by its code number SR 58360 A, m.p. 219°–221° C., [alpha]=−35° (water/ethanol 1/1, c =2%). Yield: 20% of the theoretical value.

EXAMPLE 18

To 45 ml of a 1M solution of boron tribromide in methylene chloride, there is added, dropwise, over 15 minutes, under nitrogen stream, at the temperature of −20° C. 2.5 g of a suspension of (1R,2′RS)-2-[(7-methoxy-1,2,3,4-tetrahydronaphth-2-yl)amino]-1-phenylethanol hydrochloride, obtained as described in Example 12, in 80 ml of anhydrous methylene chloride. The reacting mixture is left under stirring at the temperature of −20° C. for 3 hours and 30 minutes, then 150 ml of ice there are added and the mixture is made alkaline with concentrated ammonia. The reacting mixture is left under stirring at room temperature for 30 minutes and extracted with 300 ml of ethyl acetate. The organic phase is separated, dried, filtered and evaporated to dryness. The oil thus obtained is purified by flash-chromatography using a mixture of ethyl acetate/methanol 9/1 for the elution. The product thus obtained is dissolved in isopropyl alcohol, to the solution there is added isopropyl alcohol containing ethyl ether saturated with hydrogen chloride; the solvent is evaporated and the residue triturated with ethyl ether. The (1R,2′RS)-2-[(7-hydroxy-1,2,3,4-tetrahydronaphth-2-yl)amino]-1-phenylethanol hydrochloride, designated by its code number SR 58365 A, is thus obtained, m.p. 150°–152° C., [alpha]=−35° (water/ethanol 1/1, c=2%). Yield: 37% of the theoretical value.

EXAMPLE 19

By following the procedure of Example 18, starting from 2.5 g of (1S,2′RS)-2-[(7-methoxy-1,2,3,4-tetrahydronaphth-2-yl)amino]-1-phenylethanol phenylethanol hydrochloride, obtained as described in Example 13, the (1S, 2′RS)-2-[(7-hydroxy-1,2,3,4-tetrahydronaphth-2-yl)amino]-1-phenylethanol hydrochloride, designated by its code number SR 58364 A, is obtained, m.p. 153°–155° C., [alpha]=+37° (water/ethanol 1/1, c =2%). Yield 7% of the theoretical value.

EXAMPLE 20

To 27 ml of a 1M solution of boron tribromide in methylene chloride, there is added, dropwise over 10 minutes, under nitrogen stream, at a temperature of −18° C., 1.5 g of a suspension of the (−)-(1R)-2-[(7-methoxyl-1,2,3,4-tetrahydronaphth-2-yl)amino]-1-phenylethanol hydrochloride, obtained as described in Example 14, in 40 ml of anhydrous methylene chloride. The reacting mixture is left under stirring at the temperature of −18° C. for 6 hours, then there is added 100 ml of ice. The mixture is made alkaline with concentrated ammonia, extracted with 200 ml of ethyl acetate and the organic phase is separated, dried filtered and evaporated to dryness. The oil thus obtained is purfied by flash-chromatography using a mixture ethyl acetate/methanol 9/1 for the elution. To a solution of the product in 10 ml of isopropyl alcohol, there is added a saturated solution of hydrogen chloride in isopropyl alcohol, then 60 ml of ethyl ether. Thus, the (−)-(1R)-2-[(7-hydroxy-1,2,3,4-tetrahydronaphth-2-yl)-amino]-1-phenylethanol hydrochloride, designated by its code number SR 58374 A, is obtained, m.p. 205°–207° C. [alpha]=−91° (water/ethanol 1/1, c=2%). Yield; 17% of the theoretical value.

EXAMPLE 21

By following the procedure of Example 20, starting from 3.2 g of (+)-(1S)-2-[(7-methoxy-1,2,3,4-tetrahydronaphth-2-yl)-amino]-1-phenylethanol hydrochloride, obtained as described in Example 15, the (+)-(1S)-2-[(7-hydroxy-1,2,3,4-tetrahydronaphth-2-yl)-amino]-1-phenylethanol hydrochloride, designated by its code number SR 58372 A, is obtained, m.p. 200°–202° C. [alpha]=+89° (water/ethanol 1/1, c=2%). Yield; 30% of the theoretical value.

EXAMPLE 22

To 23.4 ml of a 1M solution of boron tribromide in methylene chloride, there is added, dropwise over 10 minutes, under nitrogen stream, at the temperature of −18° C., 1.3 g of a suspension of the (+)-(1R)-2-[(7-methoxy-1,2,3,4-tetrahydronapth-2-yl)amino]-1-phenylethanol hydrochloride, obtained as described in Example 16, win anhydrous methylene chloride. The reacting mixture is left to stand under stirring at the temperature of −18° C. for 3 hours and 30 minutes, then there is added 100 ml of ice. The mixture is made alkaline with concentrated ammonia, extracted with 250 ml of ethyl acetate and the organic phase is separated, dried, filtered and evaporated to dryness. The oil thus obtained is purified by flash-chromatography using a mixture ethyl acetate/methanol 9/1 for the elution. To a solution of the product thus obtained is isopropyl alcohol, there is added isopropyl alcohol saturated with hydrogen chloride, then it is evaporated to dryness and the residue is triturated with 60 ml of ethyl ether. The (+)-(1R)-2-[(7-hydroxy-1,2,3,4-tetrahydronaphth-2-yl)amino]-1-phenylethanol hydrochloride, designated by its code number SR S8375 A, is obtained, m.p. 175°–177° C., [alpha]=+30° (water/ethanol 1/1, c=2%). Yield: 50% of the theoretical value.

EXAMPLE 23

By following the procedure of Example 22, starting from 2 g of (−)-(1S)-2-[(7-methoxy-1,2,3,4-tetrahydronaphth-2-yl)amino]-1-phenylethanol hydrochloride, obtained as described in Example 17, the (−)-(1S)-2-[(7-hydroxy-1,2,3,4-tetrahydronaphth-2-yl)amino]-1-phenylethanol hydrochloride, designated by its code number SR 58373 A, is obtained, m.p. 177°–179° C., [alpha]=−33° (water/ethanol 1/1, c=2%). Yield: 30% of the theoretical value.

EXAMPLE 24

Capsules comprising one of the products of Examples 1 to 23, having the following compositions:
active substance: 15 mg
lactose: 120 mg
magnesium stearate: 5 mg
are prepared by mixing intimately charges of the ingredients above and introducing the mixture into hard gelatine capsules.

EXAMPLE 25

Tablets comprising one of the products of the Examples 1 to 23, having the following composition:
active substance: 20 mg
lactose: 100 mg
microcrystalline cellulose: 30 mg
dried corn starch: 40 mg
magnesium stearate: 5 mg
are prepared by crushing the active ingredient to a particle dimension of 0.4 mm size, by passing it through a 0.4 mm sieve, by mixing the crushed mixture with the other constituents and compressing to form the tablets.

In the same manner, tablets containing 40 mg of active substance are prepared.

EXAMPLE 26

By operating as described in Example 25 hereinabove, tablets having the following composition are prepared:
active substance: 50 mg
lactose: 95 mg
dried corn starch: 100 mg
talc: 4.5 mg
magnesium stearate: 0.5 mg

EXAMPLE 27

10,000 capsules with a content of active substance of 50 mg are prepared from the following constituents: 500 g of the 2-[(7-methoxy-1,2,3,4-tetrahydronaphth-2-yl)amino]-1-phenylethanol hydrochloride (SR 58279 A), 495 g of microcrystalline cellulose, 5 g of amorphous silica gel. The above constituents are well mixed and introduced into hard gelatin capsules of dimension 4.

EXAMPLE 28

A sterile aqueous solution useful for parenteral use containing the 2-[(7-hydroxy-1,2,3,4-tetrahydronaphth-2-yl)amino]-1-phenylethanol hydrochloride (SR 58306 A) and having the following composition:
SR 58306 A: 30 mg
sodium chloride: 5 mg
water for injectable preparation to: 2 ml
is prepared and introduced into sterile ampoules.

EXAMPLE 29

Suppositories comprising one of the products of the Examples 1 to 23 are prepared, having the following composition:
active substance: 50 mg
lactose: 250 mg
Witespol W 45 to: 1.7 g
The active substance is mixed with the lactose and the mixture is placed uniformly in suspension in the molten mass for suppositories. The suspension is poured into cooled moulds to form suppositories weighing 1.7 g.

EXAMPLE 30

Tablets comprising one of the products of the Examples 1 to 23, having the following composition:
active substance: 25 mg
lactose: 95 mg
dried corn starch: 45 mg
colloidal silica: 2 mg
soluble starch: 5 mg
magnesium stearate: 3 mg
are prepared by mixing the active substance with a part of the adjuvants. The mixture is granulated with a solution of soluble starch in water. After the granulate is dried, the remaining adjuvants are added and the tablets are made by compression.

We claim:

1. A compound of formula

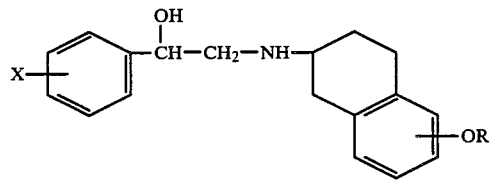

I wherein X represents hydrogen, halogen, a trifluoromethyl or a lower alkyl group and R represents hydrogen; a lower alkyl group not substituted or substituted by a cycloalkyl group containing 3 to 7 carbon atoms, a hydroxy group, a lower alkoxy, carboxy or lower carbalkoxy group; a cycloalkyl group containing 3 to 7 carbon atoms; or a lower alkanoal group; or a pharmaceutically acceptable salt thereof.

2. A compound of formula I according to claim 1 selected from the group consisting of:
2-[(7-hydroxy-1,2,3,4-tetrahydronaphth-2-yl)amino]-1-phenylethanol,
2-[(7-hydroxy-1,2,3,4-tetrahydronaphth-2yl)amino]-1-(3-chlorophenyl)ethanol,
2-[(7-carbethoxymethoxy-1,2,3,4-tetrahydronaphth-2-yl)amino]-1-(3-chlorophenyl)ethanol,
2-[(7-carbethoxymethoxy-1,2,3,4-tetrahydronaphth-2-yl)amino]-1-phenylethanol or one of their pharmaceutically acceptable salts thereof.

3. A compound according to any one of claims 1 or 2 in the form of a single stereoisomers or in the form of a mixture of stereoisomers.

4. A compound of formula I according to claim 1 selected from group consisting of
(1R,2'RS)-2-[(7-hydroxy-1,2,3,4-tetrahydronaphth-2-yl)amino]-1-phenylethanol or a pharmaceutically acceptable salt thereof
(1S,2'RS)-2-[(7-hydroxy-1,2,3,4-tetrahydronaphth-2-yl)amino]-1-phenylethanol phenylethanol or a pharmaceutically acceptable salt thereof
(+)-(1R)-2-[(7-hydroxy-1,2,3,4-tetrahydronaphth-2-yl)amino]-1-phenylethanol,
(+)-(1S)-2-[(7-hydroxy-1,2,3,4-tetrahydronaphth-2-yl)amino]-1-phenylethanol,
(−)-(1R)-2-[(7-hydroxy-1,2,3,4-tetrahydronaphth-2-yl)amino]-1-phenylethanol,
the (−)-(1S)-2-[(7-hydroxy-1,2,3,4-tetrahydronaphth-2-yl)amino]-1-phenylethanol or one of their pharmaceutically acceptable salts thereof.

5. A pharmaceutical composition comprising an effective amount of a compound as claimed in claim 1 in admixture with a pharmaceutically acceptable carrier.

6. A pharmaceutical composition according to claim 5 comprising from 0.1 to 500 mg. of a compound as claimed in claim 1.

7. A pharmaceutical composition comprising an effective amount of a compound as claimed in claim 3 in admixture with a pharmaceutically acceptable carrier.

8. A pharmaceutical composition comprising an effective amount of a compound as claimed in claim 2 in admixture with a pharmaceutically acceptable carrier.

* * * * *